US008501415B2

(12) United States Patent
Bergmann et al.

(10) Patent No.: US 8,501,415 B2
(45) Date of Patent: Aug. 6, 2013

(54) IDENTIFICATION OF TSH RECEPTOR AUTOANTIBODIES USING AFFINITY-PURIFIED ANTIBODIES

(75) Inventors: Andreas Bergmann, Berlin (DE); Sabine Costagliola, Brussels (BE); Gilbert Vassart, Brussels (BE)

(73) Assignee: B.R.A.H.M.S. GmbH, Hennigsdorf (DE)

( * ) Notice: Subject to any disclaimer, the term of this patent is extended or adjusted under 35 U.S.C. 154(b) by 186 days.

(21) Appl. No.: 10/536,577

(22) PCT Filed: Oct. 31, 2003

(86) PCT No.: PCT/EP03/12129
§ 371 (c)(1),
(2), (4) Date: May 26, 2005

(87) PCT Pub. No.: WO2004/048415
PCT Pub. Date: Jun. 10, 2004

(65) Prior Publication Data
US 2006/0165676 A1    Jul. 27, 2006

(30) Foreign Application Priority Data

Nov. 26, 2002 (DE) .................................. 102 55 144

(51) Int. Cl.
*G01N 33/53* (2006.01)
(52) U.S. Cl.
USPC ......................................................... 435/7.1
(58) Field of Classification Search
None
See application file for complete search history.

(56) References Cited

U.S. PATENT DOCUMENTS

| 6,228,597 B1 * | 5/2001 | Parmentier et al. ............. 435/7.1 |
| 6,537,760 B1 | 3/2003 | Bergmann et al. ............. 435/7.1 |

FOREIGN PATENT DOCUMENTS

| EP | 0 433 509 B1 | 11/1996 |
| WO | WO 91/03483 | 3/1991 |
| WO | WO 91/09121 | 6/1991 |
| WO | WO 91/10735 | 7/1991 |
| WO | WO 98/20343 | 5/1998 |
| WO | WO 98/26294 | 6/1998 |
| WO | WO 99/36782 | 7/1999 |

OTHER PUBLICATIONS

Morgenthaler et al. (Mol. And Cell. Endo. 2003, 212:73-79.*
Webster's II, New Riverside University Dictionary, 1984, Houghton Muffin Company, Boston, MA, USA, p. 453, left column, 14th entry.*
Weir et al. Handbook of Experimental Immunolgoy in Four Volumns, Volumn 1: Immunochemistry, Forth Edition, 1986, Blackwell Scientific Publications, Palo Alto, CA, USA, pp. 34.7-34.8.*
Morris et al. (Autoimmunity 1994, 17:287-299).*
Costagliola et al. (J Immunolo. 1998, 160:1458-1465).*
Bryant et al., "Identification of thyroid blocking antibodies and receptor epitopes in autoimmune hypothyroidism by affinity purification using synthetic TSH receptor peptides," Autoimmunity, 22, pp. 69-79 (1995).
Nagayama et al., "Binding Domains of Stimulatory and Inhibitory Thyrotropin (TSH) Receptor Autoantibodies Determined with Chimeric TSH-Lutropin/Chorionic Gonadotropin Receptors," J. of Clinical Investigation, Inc., 88, pp. 336-340 (1991).
Dallas et al., "A Region on the Human Thyrotropin Receptor which can Induce Antibodies that Inhibit Thyrotropin-mediated Activation of in vitro Thyroid Cell Function also contains a Highly Immunogenic Epitope," J. of Autoimmunity, 7,pp. 469-483 (1994).
Morgenthaler et al., "Affinity purification and diagnostic use of TSH receptor autoantibodies from human serum," Molecular and Cellular Endocrinology, 212, pp. 73-79 (2003).
Morris et al., "Identification of Epitopes and Affinity Purification of Thyroid Stimulating Auto-Antibodies Using Synthetic Human TSH Receptor Peptides," Autoimmunity, 17, pp. 287-299 (1994).
Furmaniak et al., "The Structure of Thyroid Autoantigens," Autoimmunity, 7, pp. 63-80 (1990).
Lidert et al., "Cloning, Sequencing and Expression of the Human Thyrotropin (TSH) Receptor Evidence for Binding of Autoantibodies," Biochemical and Biophysical Research Communications, 165(3), pp. 1250-1255 (1989).
Nagayama et al., "Molecular Cloning, Sequence and Functional Expression of the cDNA for the Human Thyrotropin Receptor," Biochemical and Biophysical Research Communications, 165(3), pp. 1184-1190 (1989).
Nagayama et al., "The Thyrotropin Receptor 25 Years after Its Discovery: New Insight after Its Molecular Cloning," Molecular Endocrinology, 6(2), pp. 145-156 (1992).
Costagliola et al., "Second Generation Assay for Thyrotropin Receptor Antibodies Has Superior Diagnostic Sensitivity for Graves' Disease," J. of Clinical Endocrinology and Metabolism, 84(1), pp. 90-97 (1999).
Costagliola et al., "Production of monoclonal antibodies recognizing the native human TSHR and induction of thyroiditis in Balb/c mice, by genetic immunization," J. Endocrinol. Invest. 20 (Suppl. to No. 5) (1997).
Costagliola et al., "Genetic Immunization Against the Human Thyrotropin Receptor Causes Thyroiditis and Allows Production of Monoclonal Antibodies Recognizing the Native Receptor'," J. of Immunology, 160, pp. 1458-1465 (1998).
Ochi et al., "Anti-TSH antibodies in Graves' disease and their failure to interact with TSH receptor antibodies," Acta Endocrinologica (Copenh) 120, pp. 773-777 (1989).
Sakata et al., "Anti-bovine thyrotropin autoantibodies in patients with Hashimoto's thyroiditis, subacute thyroiditis, and systemic lupus erythematosus," J. Endocrinol. Invest., 14, pp. 123-130 (1991).

(Continued)

*Primary Examiner* — Sharon Wen
(74) *Attorney, Agent, or Firm* — Heslin Rothenberg Farley & Mesiti P.C.

(57) ABSTRACT

The present invention relates to the use of affinity-purified polyclonal human autoantibodies against the TSH receptor (TSHR-Auto-Ab), obtained from the serum of Graves' disease patients and which have been purified to obtain biochemical homogeneity and comprise a specific activity of at least 1 IU/mg protein (human immunoglobulin). Also disclosed is the use of animal antibodies, which compete with the former for the binding sites of a functional human TSH receptor, as a specific binding reagent in an immunological determination method for the clinical identification of autoantibodies against the TSH receptor (TSHR-Auto-Ab) in a sample of a biological fluid of a patient to be examined for Graves' disease.

5 Claims, 5 Drawing Sheets

OTHER PUBLICATIONS

Figure 1:
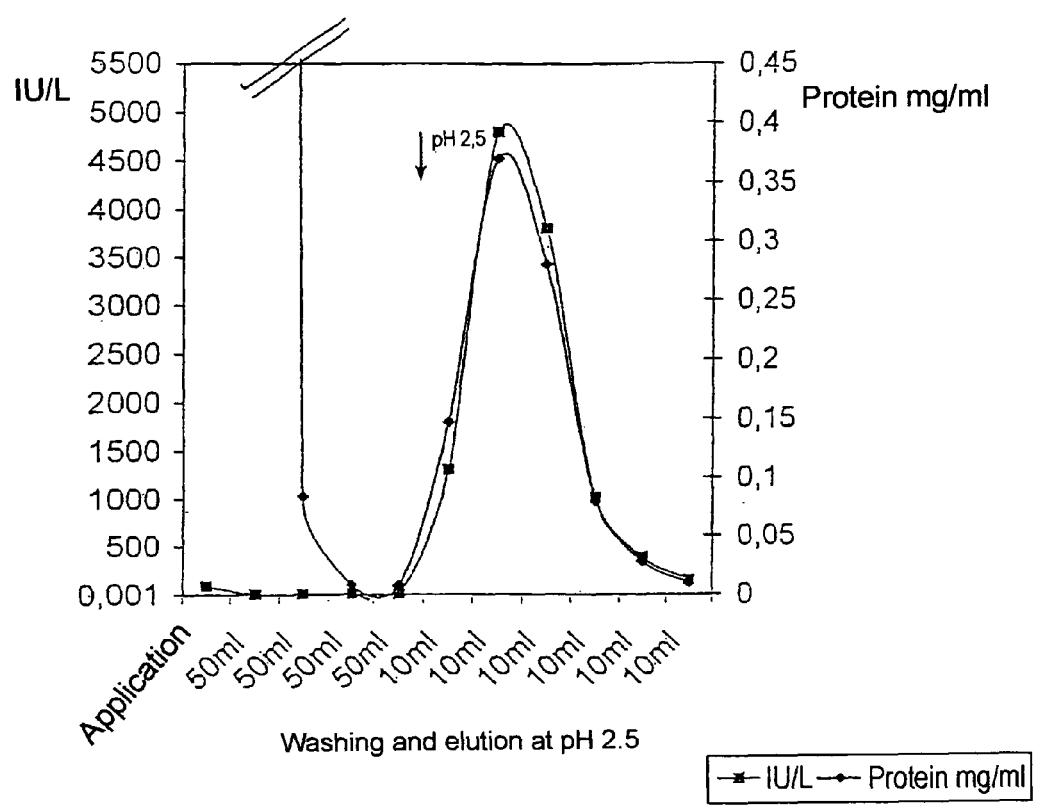

Inui et al., "Precise Determination of TSH Receptor Antibody Activity in Serum Containing Bovine TSH (bTSH) Binding Antibody by Absorption Using Denatured bTSH or Sheep FSH," Thyroid, 6(4), pp. 295-299 (1996).

Brown et al., "Partial Purification and Characterization of Thyrotropin Binding Inhibitory Immunoglobulins from Normal Human Plasma," J. of Clinical Endocrinology and Metabolism, 56(1), pp. 156-163 (1983).

* cited by examiner

IDENTIFICATION OF TSH RECEPTOR AUTOANTIBODIES USING AFFINITY-PURIFIED ANTIBODIES

CROSS REFERENCE TO RELATED APPLICATIONS

This application is a 371 filing of PCT International application no. PCT/EP2003/012129 filed Oct. 31, 2003 and published in German as WO 2004/048415 on Jun. 10, 2004 which claims the priority of German application no. 102 55 144.8 filed Nov. 26, 2002, the disclosures of which are hereby incorporated by reference in their entirety.

The invention relates to improved receptor binding assays for determining TSH receptor autoantibodies (TSHR-Auto-Ab) which occur in thyroid autoimmune diseases, in particular in Graves' disease.

It is known that numerous diseases in which the thyroid gland is involved are autoimmune diseases in which autoantibodies against molecular structures of the thyroid gland are formed and, in association with the disease, begin to act as autoantigens. The most important known autoantigens of the thyroid gland are thyreoglobulin (Tg), thyroid peroxidase (TPO) and in particular the TSH receptor (TSHR) (cf. Furmaniak J et al., Autoimmunity 1990, Vol. 7, pages 63-80).

The TSH receptor is a receptor which is localized in the thyroid membrane and to which the hormone TSH (thyroid-stimulating hormone or thyreotropin) excreted by the pituitary gland binds and thus triggers the secretion of the actual thyroid hormones, in particular of thyroxin. The TSH receptor belongs to the receptor family consisting of the G-protein-coupled glycoprotein receptors with a large amino-terminal extracellular domain, to which the LH/CG receptor and the FSH receptor also belong. An explanation of the chemical structure of the TSH receptor, i.e. of the sequence of the DNA coding for it and of the amino acid sequence of the receptor itself which can be derived therefrom, was achieved at the end of 1989 (cf. Libert F. et al., Biochem. Biophys. Res. Commun. 165: 1250-1255; Nagayama Y. et al., Biochem. Biophys. Res. Commun. 165: 1184-1190; cf. also EP-A-0433509 or WO-A-91/09121; and WO-A-91/09137; WO-A-91/10735 and WO-A-91/03483; and furthermore Yuji Nagayama & Basil Rapoport, in: Molecular Endocrinology, Vol. 6 No. 2, pages 145-156, and the literature cited therein).

It is generally assumed that stimulating autoantibodies which are formed against the TSH receptor (TSHR) and interact with this so that the thyroid gland is stimulated, which manifests itself as thyroid hyperfunction (hyperthyroidism), play a role in the thyroid autoimmune disease known as Graves' disease. However, it is known that, in addition to stimulating autoantibodies, also those which have opposite or even no clinically relevant effects and are also referred to as "blocking" or "neutral" antibodies are also found in the circulation of human patients. The determination of autoantibodies against the TSH receptor (abbreviated below to TSHR-Auto-Ab or, in association with determinations using the assays developed by the Applicant in the terminology of the latter, also to TRAK) is of considerable clinical importance for the diagnosis of Graves' disease and other thyroid autoimmune diseases.

Accordingly, assays for determining thyroid autoantibodies formed against TSHR have long been used routinely in clinical diagnosis.

In the earlier methods, it was always necessary to adopt a procedure in which the autoantibodies to be determined were allowed to compete with bovine TSH (bTSH) for binding sites of a solubilized porcine TSHR preparation, and the immune complexes formed were precipitated for a solid-liquid separation with polyethylene glycol (PEG).

The method which is described in more detail in the published Patent Applications DE 198 01 319.1 A1, WO 99/36782 based on it or patent EP 0 975 970 B1 and moreover in the publication by Sabine Costagliola et al., Second Generation Assay for Thyrotropin Receptor Antibodies Has Superior Diagnostic Sensitivity for Graves' Disease, in: *J Clin Endocrinol Metab* 84:90-97, 1999 is currently regarded as the most modern method for TSHR-Auto-Ab determination. The teachings of these publications relating to assays to be implemented in practice are the assays of the Applicant B.R.A.H.M.S Aktiengesellschaft which are commercially available under the name DYNOtest®, TRAKhuman® or LUMItest® TRAKhuman®.

Said publications DE 198 01 319.1 A1 and WO 99/36782 contain a detailed discussion of the earlier prior art and of various difficulties associated with the determination of TSHR-Auto-Ab. For a deeper understanding of the technical background of the present invention, reference is therefore expressly made to the content of said patent applications and to the scientific publications discussed therein.

The above method according to DE 198 01 319.1 A1, of WO 99/36782 based thereon and of patent EP 0 975 970 B1 is based primarily on the fact that it may be possible for the first time to immobilize a human TSHR, in particular a recombinant TSHR, without loss of functionality on the solid phase, with the result that the TSHR-Auto-Ab determination could be carried out as a heterogeneous assay and the measured signal relevant for the determination was obtained bound directly to solid phase.

In this assay too, the competitor used is as a rule labelled bTSH.

The functional rhTSHR was immobilized using a monoclonal antibody (BA8) which recognized the conformative epitopes of TSHR and is obtained by a particular method which is described by S. Costagliola and G. Vassart in J. Endocrinol. Invest. 20 (Suppl. to no. 5), Abstract 4, (1997) and in S. Costagliola et al., Genetic Immunization Against the Human Thyrotropin Receptor Causes Thyroiditis and Allows Production of Monoclonal Antibodies Recognizing the Native Receptor, in: *The Journal of Immunology*, 1998, 160: 1458-1465. According to this method, mice are immunized for the purpose of antibody formation not with a peptidic antigen but by intramuscular injection of a DNA plasmid construct coding for hTSHR. In this way, after suitable selection, new monoclonal antibodies having high affinity to the native hTSHR, which recognize at least in part, like BA8, also conformative epitopes, are obtained.

The use of a functional immobilized human TSHR which could be used in the determination in a form affinity-purified by washing in the immobilized state has various advantages and resulted in innovations with regard to assays, the following being particularly relevant:

1. If the determination is carried out as a "two-step determination" by allowing labelled bTSH to react in a downstream step with a previously formed complex of TSHR-Auto-Ab and the affinity-purified immobilized rhTSHR, separated from the original measuring solution, a possible presence of anti-bTSH-Ab known per se in the patient sample can no longer have an interfering effect.

2. Owing to the use of a human receptor, there may be a disturbance of the assay by pathologically elevated hTSH concentrations, as occur in individual patient samples. These disturbances can be neutralized by addition of certain commercially available anti-TSH antibodies to the sample-containing measuring solution, which antibodies selectively bind the hTSH and do not cross-react with the bTSH used as competitor.

3. The new discovery mentioned above under 1. makes it possible to carry out the reaction with bTSH in the second assay step using an exactly standardizable bTSH reagent free of serum.

4. A practical weakness of the assay described has proved to be the fact that the binding ability of the human recombinant TSHR used in the assay is lost relatively rapidly respect to the labelled bovine TSH used as competitor, particularly when the TSHR is provided in the liquid phase, for example bound to suspended magnetic particles, or used in solubilized form as component of homogeneous assays.

Because said method permitted binding of the TSHR-Auto-Ab and of the labelled competitor bTSH from the measuring solution directly to an affinity-purified recombinant human TSHR bound to a solid phase, however, not only is the measurement of the signal obtained simplified in practice in the desired sense compared with a precipitation assay, but the assay design can in principle be altered in that it is possible to change over from a one-step assay (a single measuring solution obtained by successive pipetting without intermediate solid-liquid separation) to a two-step assay in which the reaction of the immobilized and affinity-purified washed TSHR with the sample and the reaction with the labelled competitor bTSH are carried out in two successive steps separated from one another by a solid-liquid separation.

In spite of the use of a functional human TSH receptor, the above-mentioned method is still similar to a traditional method in that it utilizes the competition of the autoantibodies to be determined with TSH (as a rule with labelled bovine TSH). It is true that the basic possibility of using labelled antibodies which bind to the TSH receptor as a competitor in a competitive assay instead of labelled bTSH has in principle been discussed. The number of monoclonal antibodies which were produced using different antigens and by means of different immunization techniques against the complete TSHR or individual segments thereof has in the meantime become very large. However, an antibody which has the properties of stimulating antibodies, such as those postulated as a trigger of Graves' disease, has not yet been described. In practice, there was therefore still no possibility of providing an assay which uses a competitor which makes it possible to recognize the presence and amount of stimulating autoantibodies, such as those characteristic of Graves' disease, in a more relevant manner than the competitor bTSH.

It is an object of the present invention to provide a receptor binding assay for determining TSH receptor autoantibodies which does not have the disadvantages of known competitive receptor binding assays of the prior art and is of greater clinical value.

In particular, it is a further object of the present invention to design improved receptor binding assays for the identification of TSH receptor autoantibodies so that certain disturbances of the measurement by anomalous serum components are effectively excluded even in a one-step method and optimum binding of the reactants of the assay method is ensured.

It is a further object of the invention to solve the problem of the loss of the binding ability of the TSHR respect to the tracer/competitor in the liquid phase, so that the method can be carried out as a customary automated method using suspensions of magnetic particles to which the TSHR is bound, or as a homogeneous method using the so-called KRYPTOR® technique.

It is a further object of the present invention to provide the reagent kits required for carrying out such improved receptor binding assays in routine clinical diagnosis.

Said objects are achieved according to the invention by the use of affinity-purified polyclonal human autoantibodies against the TSH receptor (TSHR-Auto-Ab) from sera of Graves' disease patients, and/or of animal antibodies which compete with these for binding sites of a functional human TSH reccceptor, as a specific binding reagent in an immunological assay method for the clinical identification of autoantibodies against the TSH receptor (TSHR-Auto-Ab) in a sample of a biological fluid of a patient to be investigated for Graves' disease.

Further details for the characterization of the affinity-purified autoantibodies to be used and resulting particularly advantageous embodiments of the improved receptor binding assays are described in the subclaims; in particular in conjunction with the detailed explanations in the following description.

The object of providing a reagent kit for realizing the present invention is achieved by a preferred reagent kit according to claim 9, which, in addition to a functional TSHR as a specific binding reagent, also contains, in particular as a labelled competitor, a preparation of affinity-purified polyclonal human autoantibodies against the TSH receptor (TSHR-Auto-Ab) from sera of Graves' disease patients, and/ or of animal antibodies which compete with these for binding sites of a functional human TSH receptor.

The affinity-purified autoantibodies according to the invention can, however, also be used as a specific binder for a solubilized, optionally directly or indirectly labelled TSHR, in the form immobilized on a solid phase, for example bound to the walls of coated tubes or microparticles.

Instead of the polyclonal autoantibodies obtained from patient sera, according to the present invention it is also possible to use selected animal antibodies which compete with these for binding sites of a functional human TSH receptor, i.e. those which "mimic" the polyclonal TSHR-Auto-Ab. Such animal antibodies, in particular animal monoclonal antibodies, have not been found to date and in particular have not been identified with certainty. Bioassays in which it was investigated whether monoclonal antibodies constitute "stimulating" antibodies in the context of stimulation of cAMP production have to date given only negative results. It was therefore necessary to conclude from this that the antibodies investigated do not represent those antibodies which are to be regarded as pathogenic autoantibodies for Graves' disease.

In the introduction and in the following part of this Application, the reagents or analytes/biomolecules used are as a rule characterized by various abbreviations which—as in the above-mentioned patent applications—are always to be understood as having the following meanings, unless as an exception something different is evident to the person skilled in the art from the specific context. The use of the special data is to permit the exact description of the experiments and measurements carried out and does not mean that the results and conclusions described apply only to the special case described. Rather, numerous pieces of information from among those imparted are clearly recognizable in their more general meaning to the person skilled in the art.

| | Explanations of the abbreviations used: |
|---|---|
| TSH = | Thyroid-stimulating hormone (thyreotropin). If the abbreviation TSH is used without further additions, it relates not to a specific product, but the binding or function of the hormones is discussed in general form. |
| bTSH = | Bovine (i.e. obtained from cattle) TSH. Preparation which is used as a tracer in conventional assays for the identification of autoantibodies against the TSH receptor. |
| hTSH = | Human TSH. Occurs in serum/plasma of healthy persons only in very low concentrations of 0.2-4 mU/l. In sera of patients suffering from hypothyroidism, however, the hTSH concentration may be significantly increased. The disturbances of autoantibody measurements caused by increased hTSH levels (more than 20 mU/l) are discussed in the above-mentioned publication WO 99/36782 and neutralized by special measures. |
| TSHR = | The TSH receptor, a glycoprotein receptor anchored in the thyroid membrane. If the abbreviation TSHR is used without further additions, it represents not a specific product but the function of the receptor or its participation in the binding is discussed in general form. |
| rhTSHR = | (Recombinant) polypeptide which is produced by genetic engineering and has the amino acid sequence of a naturally occurring TSHR at least to an extent such that it can be designated as "functional human TSH receptor", which means that it behaves to a significant extent like the naturally occurring human TSHR with regard to the binding of autoantibodies against TSHR or of TSH (bTHS/hTSH). If the abbreviation rhTSHR is used without further additions, it does not represent a specific product, i.e. rhTSHR may represent any recombinant complete, more or less glycosylated polypeptide, a partial sequence of a sufficient length or a fusion product thereof produced by genetic engineering (as described, for example, in International Patent Application PCT/EP97/06121). |
| rhTSHR(imm) = | rhTSHR preparation selectively bound to (immobilized on) a solid phase. The binding can—as described in more detail below in the description—be effected via a suitable antibody but, in the case of fusion products, can also be effected via a particular peptide residue, e.g. a biotin residue. The solid phase may be the wall of a test tube (coated tube or CT technique) but may also be a suitable suspended solid phase. In order to obtain affinity-purified polyclonal autoantibodies, rhTSHR(imm) is bound to the material used for the preparation of the affinity column (cf. experimental section). |
| Ab = | Antibody |
| TSHR-Auto-Ab = | Autoantibodies against the TSH receptor which are detectable in biological samples, in particular human serum or plasma. The identification of stimulating TSHR-Auto-Ab of this type (in the literature also abbreviated to TSI = thyroid stimulating immunoglobulins) is important in particular for the diagnosis of Graves' disease. A further customary abbreviation is TRAK. |
| Anti-hTSHR-mAb = | Monoclonal antibody which binds to rhTSHR. Without further explanations, it may be sequential with regard to its binding behavior, as described, for example, in the prior Application DE 196 51 093.7, but it may also be conformative, such as, for example, BA8. |
| Anti-bTSH-Ab = | Antibodies of unclear origin which occur in human sera or plasma, react with bTSH with formation of immune complexes and thus influence the binding of bTSH to the assay components or the measured result obtained (cf. Y. Ochi et al., Acta Endocrinologica (Copenh) 1989, 120: 773-777; S. Sakata et al., J. Endocrinol. Invest. 14: 123-130, 1991; T. Inui, Thyroid, Vol. 6: 295-299, 1996). |

The immunological assay method (ligand binding test) in which the novel selective binding reagents according to the present invention are used can in principle be of any suitable type, as known to the person skilled in the art from the literature and, for example, from the above-mentioned Applications.

If a TSHR immobilized on a solid phase is employed in the assay, a plastic surface, in particular in the form of the walls of plastic test tubes for the CT technique, microparticles, magnetic particles, filters, polymer gel materials and other known solid phase substrates can be used as such a solid phase. The assay design can also be adapted so that the determination can be carried out on known automated systems (cf. for example Elecsys system from Boehringer Mannheim or ACS 180 system from Chiron).

The use of the reagents according to the invention gives rise to numerous advantages, which will be once again discussed after the experimental section. However, it should be pointed out that a particular advantage is a design as a one-step method since, owing to the homologous nature of the polyclonal autoantibodies used as a binding reagent, disturbances which will be attributable to hTSH or to bTSH binding antibodies in the sample to be measured have no importance.

A further advantage is that the labelling of the polyclonal antibodies (or of the animal antibodies mimicking them) by means of known techniques is possible with virtually any desired known labelling reagent without it being necessary to overcome the difficulties encountered in the labelling of TSH. The label may also be a part of a pair of detection markers known per se for a method in which the specific binding reagents (solubilized TSHR; competitor in the form of autoantibodies) is present in dispersed form in the liquid reaction mixture, a first labelling component which is part of a labelling system based on fluorescence or chemiluminescence extinction or amplification being bound to the antibody, and the second labeling component of this labelling system is bound to a second, non-competing antibody used for the indirect labelling of the solubilized TSHR or directly to the solubilized TSHR, so that, after binding of the labelled antibodies to TSHR, a measurable signal, e.g. a fluorescent signal, is generated, which signal permits detection of the resulting sand which complexes in the measuring solution. For this variant of the method, the longer binding capability of TSHR with respect to the autoantibody preparation according to the invention, in particular compared with the binding capability with respect to TSH, is an extremely important advantage in practice.

The present invention is explained in more detail below in its various aspects on the basis of specific embodiments and experimental results, with reference to five figures. The general explanations in relation to the experiments described are hereby expressly incorporated by reference.

The figures show the following in the form of various diagrams:

FIG. 1: The elution profiles obtained in the affinity purification of autoantibodies from sera of Graves' disease patients on washing (with 3×50 ml of PBS) and the subsequent elution (with in each case 10 ml of citric acid, pH 2.5). The antibody fraction eluted with citric acid is chemically homogeneous.

Figure 2:
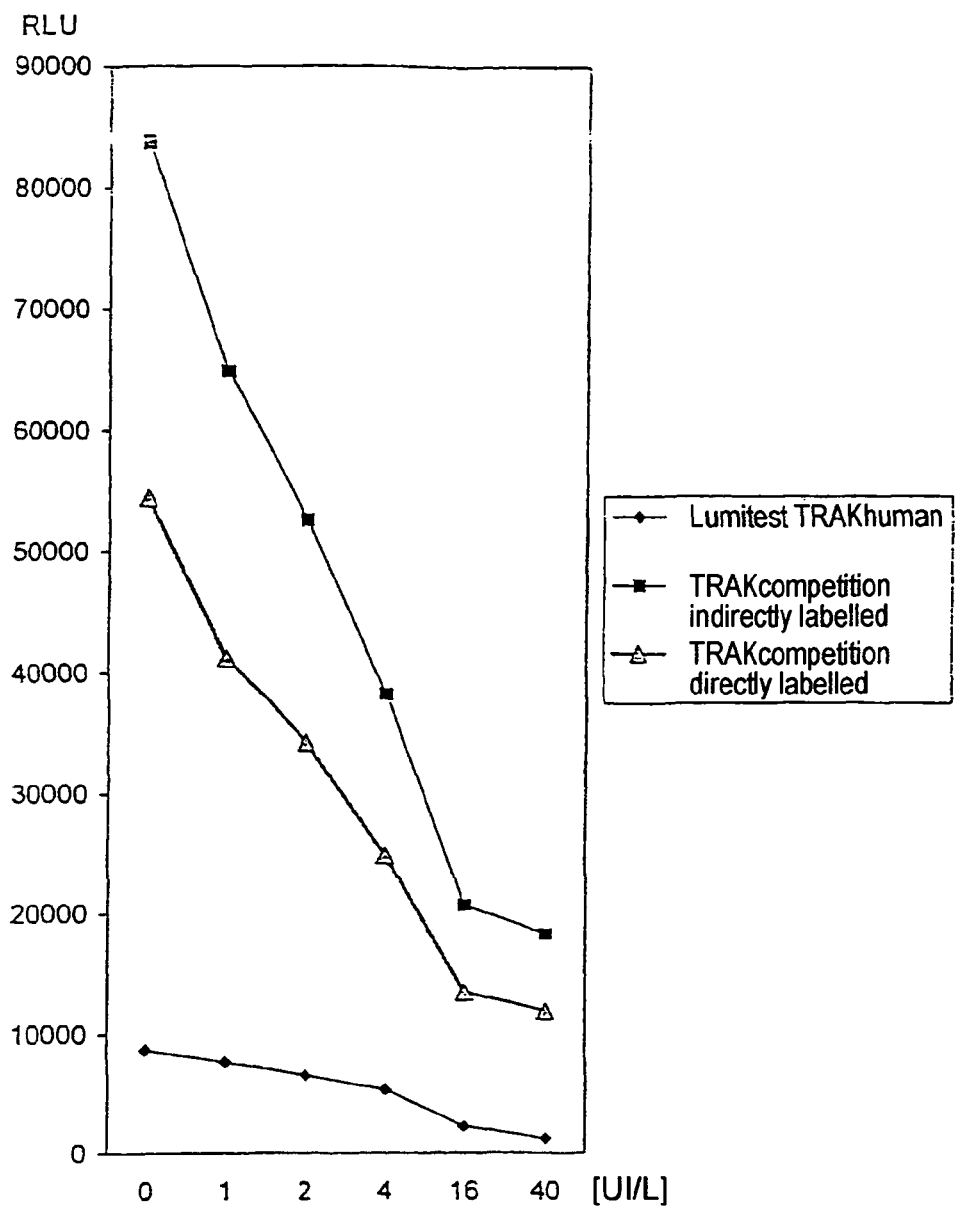

FIG. 2: Standard curves for the measurement of TSHR-Auto-Ab using affinity-purified polyclonal human autoantibodies directly or indirectly labelled with an acridinium ester, compared with the standard curve of a LUMItest® TRAKhuman® of the Applicant on the same scale for the signal strength (RLU).

Figure 3:
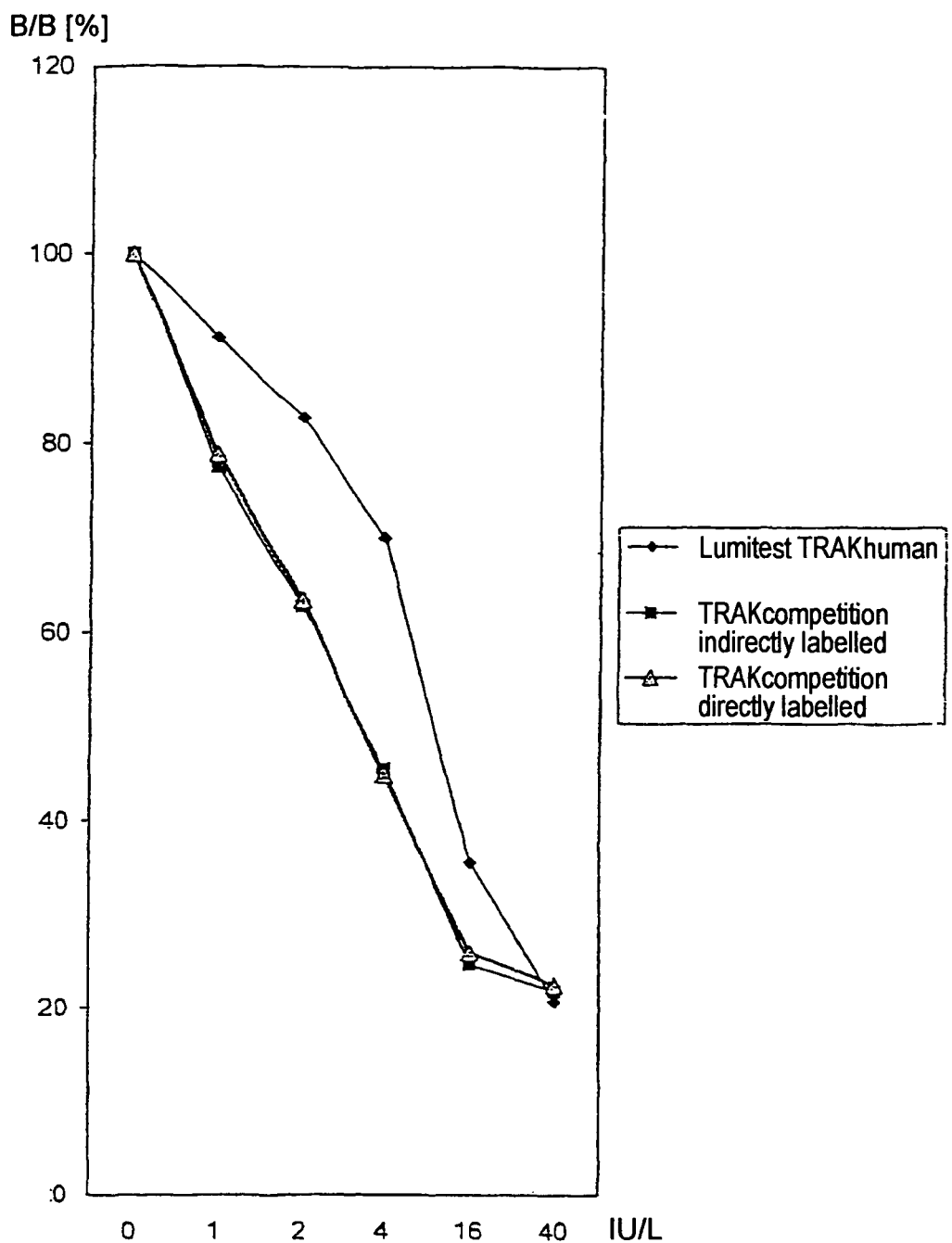

FIG. 3: The standard curves for the measurement of TSHR-Auto-Ab using affinity-purified polyclonal human autoantibodies directly or indirectly labelled with an acridinium ester, compared with the standard curve of a LUMItest® TRAKhuman® of the Applicant, based on the percentage binding ($B/B_0$).

Figure 4:
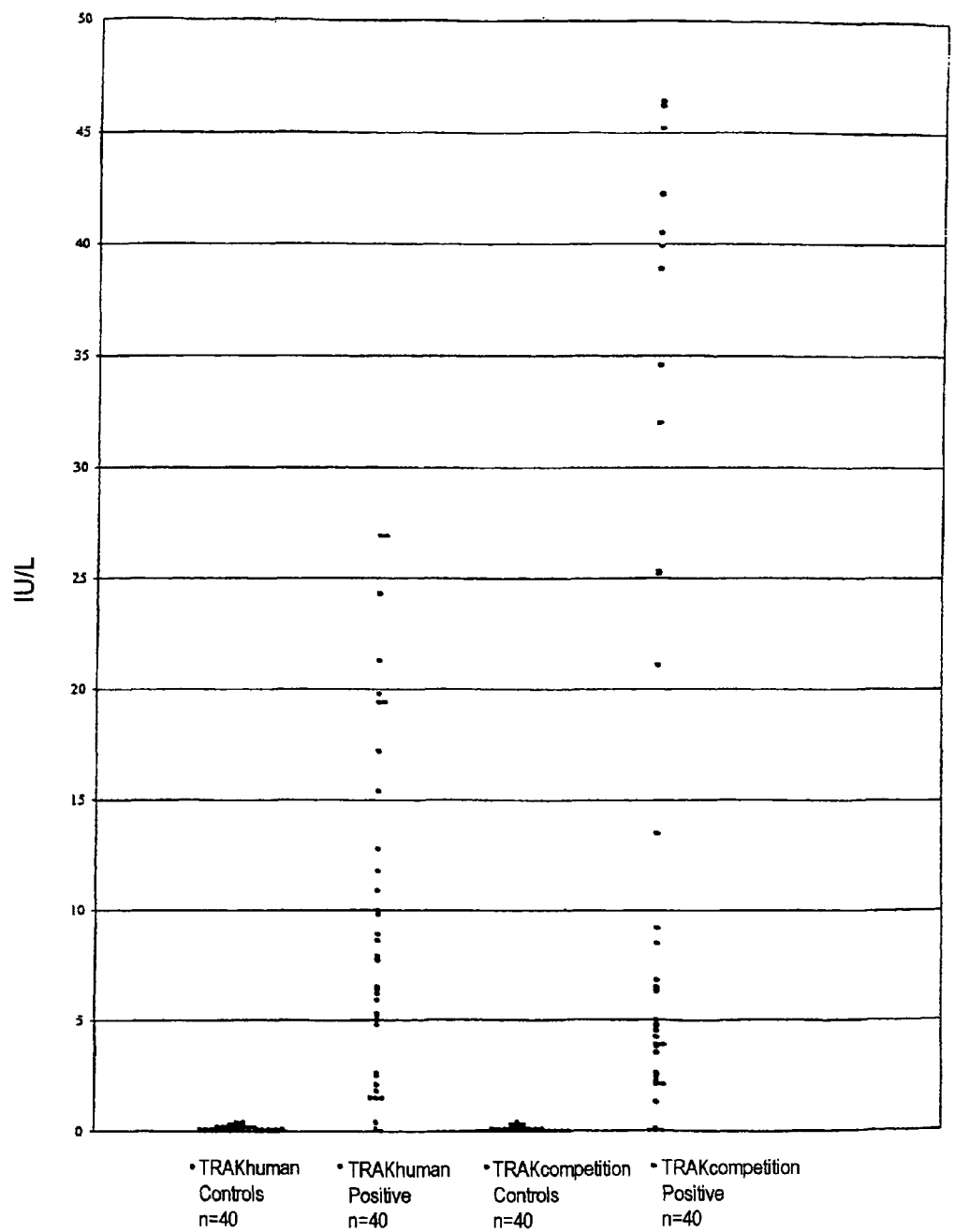

FIG. 4: The results of the measurements of patient sera (40 control sera; 40 sera of Graves' disease patients) with the aid of the LUMItest® TRAKhuman® of the Applicant (left columns) and of the test (TRAKcompetition) using labelled affinity-purified polyclonal autoantibodies from patient sera (right columns). A greater spread of the scale due to the greater signal strength and hence measurement with greater differentiation are evident.

Figure 5:
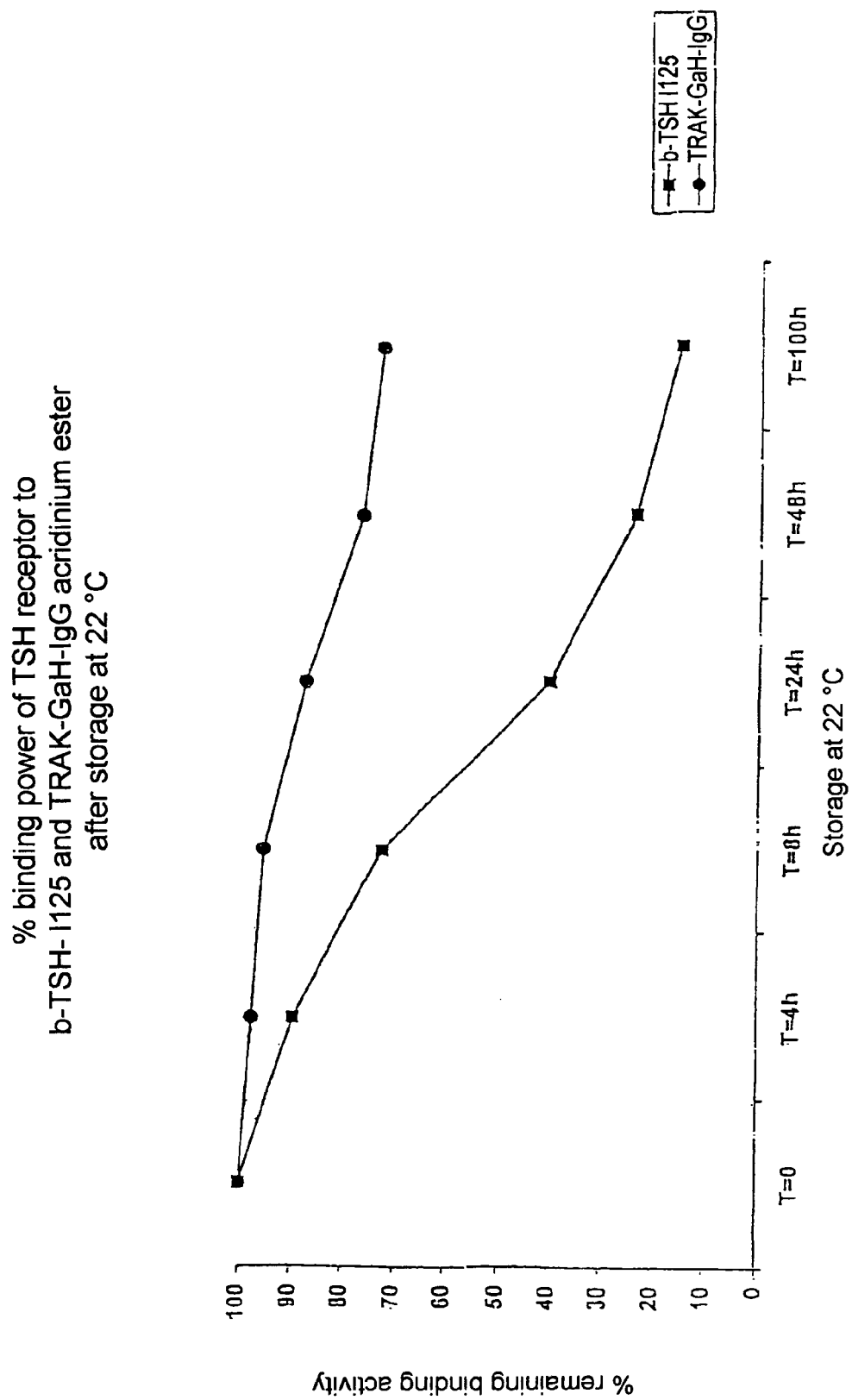

FIG. 5: Change of the binding power of a TSHR preparation to $^{125}$I-bTSH and affinity-purified polyclonal autoantibodies labelled with an acridinium ester, on storage at 22° C.

In the following description of preparation and measurement experiments, reference is made—where possible—to data to be found in the published literature when techniques or materials known per se were used:

1. Materials
1 Production of a Preparation of Affinity-Purified Polyclonal Human Autoantibodies from Sera of Graves' Disease Patients
1.1. Preparation of an Affinity Column with a Bound TSHR 20 mg of the known monoclonal conformational antibody BA8 in affinity-purified form (cf. Sabine Costagliola et al., Second Generation Assay for Thyrotropin Receptor Antibodies Has Superior Diagnostic Sensitivity for Graves' Disease, in: *J Clin Endocrinol Metab* 84:90-97, 1999; page 91, Selection of moAb by FACS; and S. Costagliola et al., Genetic Immunization Against the Human Thyrotropic Receptor Causes Thyroiditis and Allows Production of Monoclonal Antibodies Recognizing the Native Receptor, in: *The Journal of Immunology*, 1998, 160:1458-1465), 2 mg/ml in phosphate-buffered saline solution (PBS), were mixed with 50 mg of $NaIO_4$, incubated for 20 min at room temperature and then desalinated with the aid of NAP25 columns (Pharmacia), equilibrated in PBS. The protein fraction obtained (14 ml) was washed with PBS, mixed with Carbolink material (5 ml of gel; from Pierce) and incubated with gentle shaking for 20 h at 4° C.

The suspension obtained was poured onto a glass filter and washed with 200 ml of PBS. The washed Carbolink material with the antibody BA8 bound thereon was then resuspended in a solution of a recombinant human TSHR (cf. Sabine Costagliola et al., Second Generation Assay for Thyrotropin Receptor Antibodies Has Superior Diagnostic Sensitivity for Graves' Disease, in: *J Clin Endocrinol Metab* 84:90-97, 1999; page 91, Preparation of hTSH-R) (volume 250 ml, extract from $6 \times 10^9$ K562 cells) and incubated for 10 h at 4° C.

The resulting solid-phase material was washed over a glass filter 3 times with 100 ml of PBS.

1.2. Affinity Purification of Autoantibodies from Sera of Graves' Disease Patients The washed solid-phase material obtained according to 1.1 was suspended in 400 ml of a pool of sera of Graves' disease patients (mean concentration 190 U/l, total 75 U) and incubated for 10 h at 4° C. with gentle shaking.

Thereafter, the solid-phase material was introduced into a glass column (2×10 cm) closed at the bottom with a glass frit and was washed three times with 50 ml of PBS each time. The flow rate was 1 ml/min. After the last wash, the eluate was protein-free.

The elution of the autoantibodies bound via the immobilized TSHR to the solid-phase material (abbreviated to TRAK in the figure) was then effected using 10 ml portions of 50 mM citric acid at a flow rate of 1 ml/min. The column flow was collected in fractions of 1 ml.

The 1 ml fractions obtained were tested for the presence of anti-TSHR antibodies using the DYNOtest® TRAKhuman® of the Applicant, and the protein concentrations were determined by means of the BCA method. The curves which are to be regarded as being identical indicate that the amount of protein and antibody activity corresponded to one another and an antibody fraction to be designated as chemically homogeneous had been obtained.

The results are reproduced in FIG. 1 and in the table below.

TABLE 1

| Volume | TRAKhuman [IU/l] | TRAK total [IU] | Protein [mg/ml] | Protein total [mg] | Specific activity mg of protein/ 1 TRAK IU |
|---|---|---|---|---|---|
| 400 ml (donor sera) | 190 | 76 | 78 | 31200 | 411 |
| 10 ml (eluate) | 4795 | 47.95 | 0.37 | 3.7 | 0.076 |

The results show that a highly purified autoantibody preparation having high antibody activity (more than 1 IU/mg of protein) had been prepared. Such an affinity-purified preparation is not comparable with products such as those concentrated in the more distant past using preparations from thyroid membranes, for example according to Rosalind Brown et al., Partial Purification and Characterisation of Thyrotropin Binding Inhibitory Immunoglobulins from Normal Human Plasma, *J Clin Endocrinol Metab* 56: 156-162 (1983).

1.3. Labelling of the Affinity-Purified Polyclonal Autoantibodies from Graves' Disease Sera
1.3.1 Antibodies Directly Chemiluminescence-Labelled with Acridinium Ester 30 µl (100 µg) of the affinity-purified autoantibody described under 1.2. were neutralized with 70 µl of 1 M $NaPO_4$ (pH 7.2) and mixed with 10 µl of NHS acridinium ester (from Behringwerke AG, Marburg; cf. EP 0 257 541 B1; 1 mg/ml in acetonitrile) and incubated for 10 min at room temperature. Thereafter, excess acridinium active ester was saturated with 10 µl of 0.1 glycine/NaOH (pH 7.2), and unbound acridinium ester was precipitated by means of gel filtration HPLC on an SW 300 column (Millipore). All fractions of the column outflow having a UV absorption at 280 nm and 368 nm were collected. The pooled protein fraction was stored at −80° C. until required for further use in receptor binding assays.

1.3.2. Indirect Labelling by Means of a Goat Anti-Human Antibody

Alternatively to 1.3.1., the affinity-purified autoantibodies were reacted in a molar ratio of 1:1 with acridinium ester-labelled goat anti-human IgG (grade 2, Scantibodies) (100 µg of autoantibodies plus 100 µg of goat anti-human acridinium ester in 10 ml of PBS, 1% BSA). After incubation for two hours, the material was eluted to 20 ng (about 0.25 mU antibodies) per 100 µl in a buffer which consisted of PBS, 1% BSA and 10% human serum.

The two directly (1.3.1.) and indirectly (1.3.2.) labelled autoantibodies are then used as tracer in the measurements of controls and patient sera described below.

1.4 Standards

The standards used were the standards of the LUMItest® TRAK of the Applicant.

2. Assay Procedure: Pipetting and Incubation Protocols

For evaluation of the novel labelled tracer preparations based on affinity-purified autoantibodies from sera of Graves' disease patients, determinations were carried out using the following sequence of pipetting and incubation steps:

1. Pipette 100 µl of sample (patient serum, standard serum or zero standard serum) into test tubes coated with immobilized rhTSHR, from the LUMItest® TRAKhuman® of the Applicant.
2. Pipette therein directly (1.3.1) or indirectly (1.3.2) labelled affinity-purified autoantibodies, in each case 100 µl.
3. Incubate for 2 h with shaking (300 rpm) at room temperature on a Heidolph orbital shaker.
4. Pipette 1 ml of wash solution (PBS).
5. Decant.
6. Repeat steps 4 and 5 three times each.
7. Measure the acridinium ester remaining on the wall of the test tube by triggering the luminescence reaction as chemiluminescent light yield using a suitable luminometer, e.g. Berthold LB 952 T/16.
8. Determination of TSHR-Auto-Ab in patient sera.

The results of the measurement of 40 control sera and 40 patient sera with the two differently labelled autoantibody fractions are shown in FIGS. 2 and 3.

It is evident that a substantially high specific signal is obtained than in the LUMItest® TRAKhuman®, while, with regard to the diagnosis of Graves' disease, comparable or even higher sensitivity and specificity are obtained.

Surprisingly, it was furthermore found that, exactly like a solubilized TSHR, the immobilized recombinant human TSH receptor used as a specific binding partner in the determination retains its binding capability with respect to the labelled autoantibodies, and hence its suitability as a reagent for the antibody determination, substantially longer than with the use of labelled bTSH as a tracer, which represents a considerable practical advantage.

Since the assay is a so-called homologous assay in which tracer and ligand to be determined are substantially identical, disturbances due to influencing of the measurement owing to the presence hTSH are not possible—this affects the tracer binding and antibody binding in an identical manner. The tracer binding was tested at hTSH concentrations up to 500 U/L, and no interference due to the presence of hTSH was found.

3. Investigation of the Stability of the Binding Behavior of TSHR Preparations with Respect to Various Tracers The recombinant human TSHR was extracted, as described, with 2% Triton in HEPES, 10% glycerol, 10 mM EDTA, 0.5% BSA, pH 7.4, from K 562 cells and was stored as an extract at 22° C.

After the intervals shown in FIG. 5, in each case one aliquot of the TSHR suspension was added to polystyrene tubes which had been precoated with a monoclonal antibody (BA8) and was incubated for 1 h at 4° C. on an orbital shaker (Heidolph) at 300 rpm. The incubation volume was 300 µl. Thereafter, the tube was filled with HEPES buffer, pH 7.4, 0.5% BSA, the tube content was filtered with suction, and this step was repeated twice.

The bound TSHR was then stabilized by vacuum drying. The dried tubes were finally incubated with 200 µl of tracer solution from TRAKhuman® of the Applicant, which contained radiolabelled bTSH, or with 200 µl of the indirectly labelled affinity-purified autoantibody preparation prepared as described above under 1.3.2, for 2 h at 22° C. with shaking (300 rpm).

The unbound labelled material was then removed in each case by washing the tubes with PBS (addition of 2 ml of PBS/filtration with suction, repeated 3 times). The label remaining behind on the tube surface was finally measured in a gamma counter or a luminometer.

The results are shown in FIG. 5. It is clearly evident that, with increasing duration of storage, less and less labelled bTSH tracer was bound and, in the samples after storage for 100 h, the bTSH binding had been reduced to about 20% of the initial value, whereas the binding of the labelled autoantibody fraction had decreased only slightly in the same period. Since a decrease of the binding capability in a homologous assay relates to tracer and analyte equally, whereas this need not be true in the case of the binding capability relative to a bTSH tracer in comparison with the analyte, the findings means that the accuracy of measurement is very much less subject to time influences than in the case of the known assay.

4. Identification/Selection of Animal Antibodies Against hTSHR which Compete with Autoantibodies from Sera of Graves' Disease Patients for Binding Sites of a Functional Recombinant Human TSH-R Because it is by nature a homologous assay, an assay using a preparation of labelled affinity-purified polyclonal autoantibodies from Graves' disease sera as a competitor permits selection of those animal antibodies, in particular monoclonal antibodies, which actually compete with Graves' disease autoantibodies and may therefore be those having a stimulating effect, as has not yet been described to date.

Using the technique of genetic immunization according to S. Costagliola et al., Genetic Immunization Against the Human Thyrotropin Receptor Causes Thyroiditis and Allows Production of Monoclonal Antibodies Recognizing the Native Receptor, in: *The Journal of Immunology*, 1998, 160: 1458-1465, a large number of animal monoclonal antibodies against TSH-R was produced.

On testing in the homologous assay described above, it was found that, of 3000 clones tested, only 7 were capable of competing with the labelled affinity-purified polyclonal autoantibodies from Graves' disease sera. In the bioassay, the monoclonal antibodies of these 7 clones all showed stimulation of cAMP production and are therefore capable of mimicking the autoantibodies against TSH-R which occur in Graves' disease. This shows that—even if with an apparently fairly low frequency—it is actually possible to produce monoclonal antibodies which correspond in their binding behavior to the natural autoantibodies and can therefore be used alone or as a mixture thereof or in a mixture or combination with affinity-purified autoantibodies as specific binding reagents (competitor/tracer; solid-phase component; secondary competitor) for the diagnosis of Graves' disease, for example instead of the antibodies which can be obtained from patient sera by affinity purification.

The invention claimed is:

1. A method for determining the amount of thyroid stimulating hormone (TSH) receptor autoantibodies in a human serum or plasma sample comprising:
   a) contacting said human serum or plasma sample with a functional TSH receptor (TSHr) that is immobilized on a solid support in the presence of labeled autoantibodies against the TSH receptor for a time sufficient for the autoantibodies in said human or plasma sample to competitively bind to the TSH receptor;
   b) removing unbound labeled TSH receptor autoantibodies; and
   c) determining the amount of TSH receptor autoantibodies in the human serum or plasma sample by measuring the amount of labeled autoantibodies bound to the TSH receptor,
wherein the labeled autoantibodies against the TSH receptor are polyclonal human autoantibodies from a pool of sera from human Graves' disease patients that are affinity purified using a recombinant human TSH receptor that is immobilized to a solid support by a selective monoclonal antibody that:
   (i) recognizes a conformational epitope of the functional human TSH receptor;
   (ii) does not bind to peptides representing short sequences of human TSH receptor but binds strongly to complete functional recombinant human TSH receptor; and
   (iii) is obtained by immunizing an animal with a DNA construct that encodes the human TSH receptor.

2. The method of claim 1, wherein the affinity-purified polyclonal human autoantibodies against the TSH receptor are purified to biochemical homogeneity and have a specific activity of at least 1 IU/mg of protein.

3. The method of claim 1, wherein the affinity-purified polyclonal human autoantibodies against the TSH receptor are obtained by purification by affinity chromatography, from a pool of sera of Graves' disease patients, wherein said autoantibodies are bound to an affinity material having a functional human recombinant TSH receptor bound thereto, washed to remove unbound autoantibodies and then eluted from the affinity material.

4. The method of claim 1, wherein said affinity-purified polyclonal human autoantibodies against the TSH receptor are labeled with a radioisotope, a chemiluminescent label or a fluorescent label.

5. The method of claim 4, wherein said affinity-purified polyclonal human autoantibodies against the TSH receptor are directly or indirectly labeled.

* * * * *